United States Patent [19]
Claus et al.

[11] Patent Number: 5,597,701
[45] Date of Patent: Jan. 28, 1997

[54] PROCESS FOR DETERMINING ANDROSTENONE CONTENTS IN ADIPOSE TISSUES

[75] Inventors: Rolf P. Claus, Stuttgart; Martin Dehnhard, Waldenbuch, both of Germany

[73] Assignee: Riedel-De Haen Aktiengesellschaft, Germany

[21] Appl. No.: 397,099

[22] PCT Filed: Aug. 31, 1993

[86] PCT No.: PCT/EP93/02350

§ 371 Date: Mar. 7, 1995

§ 102(e) Date: Mar. 7, 1995

[87] PCT Pub. No.: WO94/06018

PCT Pub. Date: Mar. 17, 1994

[30] Foreign Application Priority Data

Sep. 8, 1992 [DE] Germany .................... 42 29 904.7

[51] Int. Cl.$^6$ .................... G01N 33/53; G01N 33/537; G01N 33/543; G01N 33/48
[52] U.S. Cl. .................... 435/7.93; 435/7.9; 435/7.92; 436/63; 552/650; 552/638; 552/640; 552/641; 552/624; 552/625; 552/633
[58] Field of Search .................... 435/7.92, 7.9, 435/7.93; 436/63; 552/650, 638, 640, 641, 624, 625, 633

[56] References Cited

PUBLICATIONS

Archiv Für Lebensmittelhygiene, "Determination of the boar steroid 5a–androst–16–en–3–one in adipose tissue of pigs with a rapid microtitre plate enzyme–immunoassay (MTE)", vol. 39, No. 4, Jul., 1988, pp. 87–90.

Chemical Abstracts, Abstract No. 158023, "Quantitative determination of the boar taint substance 5.alpha–androst–16–en–3–one in fat", vol. 85, No. 21, Nov. 22, 1976, p. 386.

Chemical Abstracts, Abstract No. 55921, "A method for the rapid determination of the boar taint steroid androstenone [in the adipose tissue of swine]", vol. 111, No. 7, Aug. 14, 1989, 608.

Chemical Abstracts, Abstract No. 4049, "Method for determination of the odorous substance 5.alpha–androst–16–en–3–one in boar fat", vol. 83, No. 1, Jul. 7, 1975, p. 368.

Journal of Agricultural and Food Chemistry, "Monoclonal Antibody–Based Enzyme–Linked Immunosorbent Assay for C19–delta16–Steroids in Sera of Boar Pigs", vol. 38, No. 1, Jan. 1990, pp. 331–335.

Primary Examiner—Toni R. Scheiner
Assistant Examiner—Sheela J. Huff
Attorney, Agent, or Firm—Connolly & Hutz

[57] ABSTRACT

A process and appropriate device are disclosed for determining the androstenone content of adipose tissues in clearly shorter times. The disclosed process has the following steps: (a) liquefying an adipose tissue sample by heating up to a predetermined temperature in the 45° to 60° C. range; (b) mixing a defined amount of the liquid fat with a water-soluble solvent for androstenone at the temperature of the liquid; (c) cooling the fat/solvent mixture down to a predetermined temperature, at which a substantial proportion of the fat dissolved in the solvent is separated from the solution whereas the major part of the androstenone dissolved in the solvent phase remains dissolved in the solvent; (d) sampling of a defined amount of the androstenone-containing solvent phase and diluting it in a predetermined ratio with an aqueous buffer solution admissible for the used detection process; (e) determining the androstenone content of the solvent/buffer solution phase by means of known per se competitive immunological detection reactions.

14 Claims, No Drawings

PROCESS FOR DETERMINING ANDROSTENONE CONTENTS IN ADIPOSE TISSUES

The invention relates to a process for determining androstenone contents in adipose tissues and to a device for carrying out this process.

5α-Androst-16-en-3-one, which is responsible for the sexual odor of the boar and has an intense urine-like odor, accumulates in the adipose tissue of the animals. This accumulation in the fat does not depend on the anatomical position of adipose tissue and affects equally, for example, subcutaneous fat (back fact), intermuscular fat, intramuscular fat and organ fat. This results in the considerable problem that meat from boars may cause, especially on heating during preparation, an odor of urine which is organoleptically extremely unpleasant. On the other hand, because of the anabolic effect of the hormones which are likewise, besides androstenone, produced in the testis, boars show considerable growth advantages. The approval of boar fattening within the EC demands a possible investigation in order to be able routinely to identify and cull those boars in which, because of advanced pubertal development, the deposition of sexual odor in the fat has already reached a very high level. Currently, the limit for the androstenone content which is still tolerable is suggested to be 0.5 μg/g of adipose tissue.

Although reliable measurement processes, in particular with an enzyme-immunological bases, for determining androstenone in adipose tissue have already been disclosed to data, the known processes permit at the most laboratory investigations on random samples, but by no means continuous monitoring in parallel with the slaughter line because of the very long time required for the analyses.

It is an object of the invention to improve the known measurement processes so far that they can be carried out in a considerably shorter time and, if possible, can also be applied in a technically simple, automatable process.

This object is achieved according to the invention in a process of the type described at the outset by the determination process comprising the following steps:

a) liquefying an adipose tissue sample by heating at a predetermined temperature in the range from 45° to 60° C.;

b) mixing a defined amount of the liquid fat with a water-soluble solvent for the androstenone at the temperature of the liquid fat;

c) cooling the fat/solvent mixture to a predetermined temperature at which considerable proportions of the fat dissolved in the solvent on the one hand are separated out of the solution, and on the other hand however the predominant part of the androstenone dissolved in the solvent phase remains dissolved in the solvent;

d) removing a defined amount of the androstenone-containing solvent phase and diluting in a predetermined ratio with an aqueous buffer solution which is suitable for the detection process used;

e) measuring the androstenone content in the solvent/buffer solution phase by means of competitive immunological detection reactions known per se.

A particularly suitable detection process is represented by the measurement process which has been disclosed in the publication by R. Claus, G. Mahler and E. Münster in "ARCHIV FÜR LEBENSMITTELHYGIENE", volume 39, number 4/1988, pages 87–90. Reference is hereby made to the entire contents of this description of the competitive immunological measurement process.

Said immunological measurement process is based on a defined amount of specific antibodies raised against the substance to be measured (in this case the androstenone) being initially present in a test system. For improved manipulation of the antibodies, they are immobilized on a receptacle plate, in particular a microtitre plate. The receptacle plate prepared in this way is incubated with an enzyme-labeled androstenone and with the solvent-containing buffer solution which contains the free androstenone to be determined. After the predetermined incubation time has elapsed, decantation is carried out and androstenone not bound to the antibodies is removed from the receptacle plate.

The proportion of enzyme-labeled androstenone present on the immobilized antibodies bound to the receptacle plate depends directly on the proportion of free androstenone which was present in the solvent-containing buffer solution. The enzyme activity measurable after the process step just described results from the proportions of enzyme-labeled androstenone bound to the antibodies and is thus a measure of the extent to which the enzyme-labeled androstenone has been displaced by free androstenone introduced by the solvent-containing buffer solution.

It is then possible by means of known enzymatic reactions, for example by means of enzymatic oxidation or reduction reactions with dyes, to obtain an easily measurable variable for the presence of enzyme-labeled androstenone on the receptacle plate.

This method is also explained in detail by means of an example hereinafter.

Alternative competitive immunological detection reactions are also, of course, suitable for the process according to the invention.

It is crucial for the utilizability of the process according to the invention in automatic measurement systems which can be operated in parallel with the slaughter line that a minimum of sample-preparation steps is used and that, in particular, lengthy drying, concentration or other distillation steps are avoided.

The avoidance of such steps also promotes the reliability of the process because the androstenones have, besides their extremely good fat solubility, also a relatively high volatility, for which reason, on the one hand, low temperatures are used where possible and, on the other hand, a method which avoids drying and distillation steps increases the reliability of the analytical results.

The solvent is preferably chosen so that it has besides good dissolving properties for the androstenone to be detected in the temperature range from about 20 to about 60° C. a temperature coefficient for the rat solubility which is larger than the temperature coefficient for the androstenone solubility in this temperature range. This permits proportions of fat dissolved in the solvent to be separated out efficiently by a cooling step after mixing the liquid fat sample with the solvent so that later, in the step of mixing the solvent phase with the aqueous buffer solution, essentially no further separation out of fat droplets or, generally, of a fat phase is observed. However, at the same time, the androstenone present dissolved in the solvent remains present in the solution when the mixture is cooled and is thus available for the later detection reaction.

To minimize the interference with the later enzyme reaction used in the detection reaction system, the solvent ought preferably to have at the most a small effect on the enzyme activity.

It is furthermore desirable that the solvent has scarcely any effect on the antigen/antibody reactions in the detection reaction system in order not to reduce the selectivity and sensitivity of the detection system.

Methanol-containing solvents have proven to be particularly suitable solvents, and it has emerged, surprisingly, that, in particular, pure methanol is outstandingly suitable for the process according to the invention. Surprisingly, the methanol which is carried out into the following steps has scarcely any effect on the enzyme activity in the detection reaction system and moreover leaves the antigen/antibody reaction system essentially unaffected.

This is particularly true when the mixing ratio of the liquid fat sample to the solvent is chosen in the range from 1:10 to 0.1:10 (ratios by volume). The stated range of the mixing ratio of liquid fat sample to solvent ensures that, on the one hand, sufficient fat phase is available for extraction of the androstenone so that sufficiently small proportions of solvent phase can be used in the following step. The limits within which the invention is practicable of course depend not inconsiderably on the choice of the solvent and, of course, furthermore on the choice of the detection reaction system too.

A particularly suitable working range has proven to be a mixing ratio of liquid fat sample to solvent in the range from 0.2:10 to 0.5:10.

Another important step in respect of the possible disturbance or influencing of enzymatic reactions or of immunological reactions is the ratio of the dilution of the solvent phase with the buffer solution. This is preferably carried out in the ratio from 20:80 to 5:95 by volume so that, on the one hand, it is ensured that not too much solvent is carried over into the reaction medium in which the antigen/antibody reaction then takes place and, on the other hand, it is ensured that sufficient androstenone is available for the competing situation with the enzyme-labeled androstenone so that in the end the required detection limit can be complied with.

Particularly in respect of the dilution step, even in the cooling step the final temperature of the sample after the cooling is chosen so that the fat which is initially dissolved in the solvent during the mixing with the liquid fat sample is separated out of the solvent to such an extent that an essentially fat phase-free solution is obtained in the subsequent dilution step (step d)). If during this mixing of solvent and aqueous buffer solution extensive separation out of a fat phase were to occur, it is to be expected that this process will prevent the later detection reactions, in particular also the photometric determination of the enzyme activity.

The detection process for androstenones which has already been described previously in detail and which is published in the publication in "ARCHIV FÜR LEBENSMITTELHYGIENE" 1988, pages 87–90, was modified in particular in one pint, namely in the temperature at which the immobilized antibodies are incubated with the enzyme-labeled and free androstenone.

The detection process which is preferred in step e) of the process according to the invention can be characterized by the following steps:

(1) that a receptacle plate is coated with an antibody serum, and the antibodies are immobilized on the receptacle plate, with the antibodies reacting specifically with androstenones, in particular 5α-androst-16-en-3-one;

(2) that the immobilized antibodies are incubated simultaneously with a defined amount of an enzyme-labeled androstenone and with a predetermined volume of the solvent-containing buffer solution obtained in step d) at a temperature of about 42° to 48° C., preferably at about 45° C., for a predetermined time;

(3) that the unbound enzyme-labeled and free androstenone is removed and the coated receptacle plate is washed;

(4) that a buffer solution containing a substrate is placed on the receptacle plate, whereupon the substrate enters into an enzyme reaction with the marker enzyme;

(5) that the enzyme reaction is carried out for a predetermined time at a predetermined temperature and then stopped with a suitable reactant; and (6) that the reaction conversion of the enzymatic reaction is determined, preferably by photospectrometry.

It has emerged in this connection that, contrary to earlier practice in which this incubation was carried out at 37° C., despite the high volatility of androstenone it is possible to use a significantly higher temperature, namely in a temperature range from about 42° to 48° C. A temperature of about 45° C. is preferably maintained, at which, under the conditions defined above, a minimal time is required for the incubation while the reliability of detection is adequate.

Another advantage of the process according to the invention is that, because of the lack of separation steps and because of the careful choice of the solvent used, with the possibility of the latter being carried out into the antigen/antibody reaction systems, the further processing of the individual solutions and liquid mixtures is possible simply by pipetting. This creates the possibility of confining the transport, the mixing and separation of phases etc. to pipetting steps which can easily be automated. Furthermore, the process according to the invention produces only very small amount of liquid waste materials and waste water which must be disposed of. In addition, these can be utilized without special precautions and, for example, passed to the sewer.

A suitable device for carrying out the process according to the invention automatically is provided by a programmable and temperature-controllable pipetting device known per se which is additionally equipped with a heatable sample input station which receives the adipose tissue sample on the input side and liquefies it at the required temperature.

The pipetting device is equipped with a plurality of sample reception devices, in particular microtitre plates, and carries out process steps b), c) and d) and, where appropriate, additional steps 2, 3, 4 and 5 of the sample-preparation process and of the detection process while maintaining defined temperature conditions and time durations for the individual process steps.

On the output side, the pipetting device is equipped with a measuring device for direct or indirect determination of a measured variable reflecting the androstenone content of the adipose tissue sample.

Calibration of the measured results takes place preferably by carrying out the process steps provided for the sample to be investigated under identical conditions but using melted pig fat with defined proportions of added androstenone. In this way it is possible to compensate for all parameters and errors intrinsic to the device and typical of the process because the sample content is subsequently measured on the basis of the measurement plot obtained with the calibration substance.

The invention furthermore relates to the use of a receptacle plate on which a defined amount of specific antibodies against androstenone is immobilized for receiving the androstenone-containing sample obtained in step d) of the process according to the invention, together with an enzyme-labeled androstenone, and for subsequently carrying out the competitive detection reaction according to step e) of the process according to the invention. In this connection a receptacle plate which is designed as microtitre plate is preferably used.

The competitive immunological detection reaction used in the process according to the invention has the advantage of extremely high specificity for the substance to be measured. However, physiological reaction conditions must be ensured for these detection reactions to take place unimpaired, for which reason the preceding preparation and purification steps have considerable importance. These process steps must on the one hand isolate the substance to be measured from the biological matrix (in this case adipose tissue) and moreover ensure that no losses of substance to be measured occur owing to the ready volatility of androstenone. On the other hand, it must be ensured that no contamination is carried over into the detection reaction system (for example reagent residues, lipids from the sample etc.) which are suitable for creating non-physiological situations or else interfering in other ways with the measurement system, in particular also the photometric determination, which is preferably used, of the reaction result. The process according to the invention now provides a completely new process for sample extraction and purification with the advantage that androstenone is, despite its lipophilic properties, transferred from the adipose tissue sample into the aqueous measurement system, and simultaneously contamination with interfering lipids and androstenone losses because of its volatility are avoided.

Essentially pure methanol has proven most suitable as solvent for the extraction from the adipose tissue sample. After the methanol, which has initially been heated to the temperature of the liquid adipose tissue sample, is cooled, the solubility of the contaminating lipids decreases and they sediment as fat droplets [lacuna] the bottom of the reaction vessel, in particular the test tube, or adsorb on the glass surface. An aliquot of the cooled methanol phase which is free of fat particles is diluted with a volume suited thereto of an aqueous test buffer system. This mixture can be transferred according to the invention directly into the enzyme immunological microtitre system.

To achieve particularly reliable values, it is also in particular particularly important for there to be accurate suiting between the volumes of liquid fat, warm methanol and the ratio of the aliquot of cooled methanol to the test buffer solution. Only careful suiting of all the volumes ensures that the proportions of lipids and methanol which still in certain amounts reach the detection reaction system do not interfere under the chosen conditions with the progress of the immunological and of the enzymatic subsequent reaction.

This is particularly important when the limit aimed at is from 0.5 µg/g to 0.7 µg/g of adipose tissue. Because of the novel process according to the invention and here in particular owing to the novel type of preparation of the adipose tissue sample, it is ensured, in contrast to all other processes disclosed for the preparation and isolation of substances to be detected (including androstenone) from tissues, that all the steps can be carried out with the aid of pipetting procedures. This results in, on the one hand, avoidance of, in particular, the time-consuming evaporation of solvents or centrifugation steps and, on the other hand, the possibility of using process-controlled automatic pipettors and commercially available microtitre components.

Checking of the measurement process according to the invention on one day (examination of intraassay variance) and on several days (intraassay variance) produced the values indicated in Table 1. Reference may be made in this connection in particular to the variances in the region of the detection limit of 0.5 µg/g of adipose tissue, which are 15% (intraassay variance) and 10% (intraassay variance).

The results measured by the process according to the invention have been compared with measurements by the known standard test process (reference method according to "ARCHIV FÜR LEBENSMITTELHYGIENE" 1988, page 87–90), and revealed a very good agreement of the measurements in the rapid test or rapid process according to the invention with those in the reference process (r=0.96; p<0.0001). The averages for all 124 measured samples were 0.72 µg/g of adipose tissue for the reference process and 0.71 µg/g according to the rapid test.

TABLE 1

Precision and intra- and interassay coefficients of variation (CV) for the measurement of androstenone in fat

| Fat samples with additions of androstenone (µg/g) | Intraassay (n = 14) Mean | CV | Interassay (n = 10) Mean | CV |
| --- | --- | --- | --- | --- |
| 0.1 | 0.09 | 12% | 0.09 | 20% |
| 0.2 | 0.23 | 9% | 0.23 | 14% |
| 0.5 | 0.54 | 10% | 0.44 | 15% |
| 0.75 | 0.88 | 8% | 0.72 | 9% |
| 1.0 | 1.14 | 11% | 1.08 | 8% |
| 1.5 | 1.64 | 14% | 1.67 | 16% |

| Biological samples | Intraassay (n = 16) Mean | CV | Interassay (n = 12) Mean | CV |
| --- | --- | --- | --- | --- |
| No. 1 | 0.22 | 8% | 0.23 | 19% |
| No. 2 | 0.42 | 9% | 0.48 | 15% |
| No. 3 | 0.88 | 9% | 0.88 | 12% |

Average intraassay CV: 10%
Average interassay CV: 14%

TABLE 2

| Process | Practicability Sample throughput per hour |
| --- | --- |
| Conventional (cannot be automated) (Claus et al. 1988) | 25 |
| Process according to the invention (manual) | 75 |
| Process according to the invention (automated) | 540 |

Table 2 shows the time advantage achieved by the method according to the invention compared with the known reference method. Whereas a maximum of 25 samples/hour can be processed with the reference method, the novel determination process according to the invention permits about 75 samples/hour to be processed even when carried out manually. The sample throughput can be drastically increased on use of a completely automated measurement process, for example to more than 500 samples/hour using known automatic pipettors.

The determination process according to the invention is explained in detail hereinafter, including an explanation which goes into detail of a preferred detection measurement system.

Scheme 1: Sample extraction and purification for automatable measurement of 5α-androst-16-en-3-one ("sexual odor") in adipose tissue from pigs (Steps 1–4 comprise sample preparation, Steps 5–10 comprise the immunological measurement).

Step 1: Heat about 2 g of adipose tissue by microwave: 4 min at 180 W

Step 2: Remove 25 µl of liquefied fat by pipette in such a way that no cooling occurs, and homogenize in 1 ml of methanol Step 3: Cool to room temperature, after a few minutes remove 100 µl by pipette and dilute with 900 µl of buffer (0.04M sodium phosphate; 0.15M NaCl; 0.02% thimerosal; 0.1% BSA; pH 7.3)

Step 4: Pipette 100 μl of this methanolic buffer into a reaction well of the microtitre plate (coated with 150 μl of antiserum 1:4,000 against androstenone-3-CMO-BSA).

Step 5: Addition of androstenone-3-CMO-HRP (12 ng/25 μl of buffer)

Step 6: Incubation: 30 min at 45° C.

Step 7: Tip out, wash the plate with detergent (6×)

Step 8: Addition of 150 μl of substrate buffer

Step 9: Enzyme reaction: 15 min at 15°–20° C.

Step 10: Stop the reaction with $H_2SO_4$, measure the extinction at 450 nm

Re Step 4: Preparation of the antiserum

1. Antigen synthesis

5α-Androstenone is, as a steroid, too small to induce the formation of antibodies in the body. It must therefore be chemically coupled to a large carrier protein (bovine serum albumin=BSA) so that 5α-androstenone is recognized as antigen. For the antigen synthesis, 100 mg of androstenone are dissolved in ethanol and, after addition of 150 mg of )-carboxymethylhydroxylamine, boiled under reflux at pH 12 for four hours. The resulting 3-oxime derivative (androstenone-3-CMO) is isolated after acidification to pH 1 by precipitation thereof (the supernatant is discarded).

To couple the oxime derivative to BSA, 49.5 mg of androstenone-3-CMO are dissolved together with 58 mg of carbodiimide in 1.5 ml of dioxane. After 35 min at room temperature, 44.2 mg of bovine serum albumin in buffer (0.04M Na phosphate, 0.15M NaCl, 0.02% (w/v) thimerosal, pH 7.2) are added dropwise thereto. After 24 h at room temperature, the product is dialyzed and subsequently lyophilized (yield: about 79 mg of androstenone-3-CMO-BSA).

2. Immunization and obtaining of antiserum

For this, female rabbits are immunized with androstenone-3-CMO-BSA. This entails in each case 2 mg of the antigen being taken up in 1 ml of water and mixed with 1 ml of complete Freund's adjuvant (emulsion) and administered in 0.5 ml portions distributed over four injection sites (2×subcutaneous, 2×intramuscular). The injections are repeated every 3 weeks until a sufficient amount of antibody has been formed. The amount of antibody is determined under standard conditions. This entails serial dilutions of the serum in buffer being prepared, and the dilution which still binds 50% of a standardized amount of radioactively labeled 5α-androstenone being determined.

3. Isolation of the immunoglobulin G(IgG) fraction from the antiserum

Antibodies against 5α-androstenone-3-CMO-BSA are a component of the IgG fraction of the blood and must be isolated selectively for the enzyme immunological test described.

For this, the IgG fraction is precipitated by adding 180 mg of ammonium sulfate to 1 ml of antiserum. After 4 h at room temperature, the precipitate is centrifuged down and, after discarding the supernatant, dissolved in 5 ml of phosphate buffer (see 1.) and dialyzed against water. This IgG fraction (volume 10 ml) is used after appropriate dilution to coat the wells of the microtitre plates.

Re Step 5: Synthesis of the androstenone-enzyme conjugate

In the enzyme immunoassay used, 5α-androstenone-CMO is coupled to horseradish peroxidase (HRP). 1 mg of steroid derivative is dissolved in 1 ml of dimethylformanide [sic] and, after addition of 6.25 μl of methylmorpholine, stirred at 0° C. for 4 min. After the temperature has been reduced to −15° C., 6.25 μl of isobutyl chloroformate are added and, after a further 3 min, 20 mg of HRP dissolved in 2 ml of water. The reaction takes place at pH 8.0 and at −15° C. for one hour and subsequently at 0° C. for a further 2 h. Addition of 10 mg of $NaHCO_3$ is followed by dialysis against water (24 h), and subsequently the product is lyophilized and purified on Sephadex G-25. The enzyme conjugate (MW about 44,000) elutes with the exclusion volume of a column (proteins >25,000 are excluded) and is thus separated from low molecular weight substances (see 1. for buffer system).

The conjugate concentration per ml is subsequently determined by protein determination with HRP as calibration plot. The conjugate concentration for the test is adjusted by dilution with buffer (for example 12 ng/25 μl, see Scheme 1, Step 5).

Re Step 7: Detergent 0.02% (v/v) Tween 80 in water (double-distilled).

Re Steps 8–10: Detection of the bound enzyme

After tipping off and washing the plate with detergent (0.05% (v/v) Tween 80, in water) the substrate buffer composed of 0.1M sodium acetate, 0.004% (v/v) $H_2O_2$, 0.01% (w/v) 3,3',5,5'-tetramethylbenzidine, pH 5, is added.

After incubation at 15°–20° C. for 15 minutes, the reaction is stopped by adding 25 μl of 4N sulfuric acid (Step 10), after which the optical measurement of the dye formed depending on the amount of enzyme follows.

We claim:

1. Process for determining androstenone contents tissues, which comprises the following steps:

a) liquefying an adipose tissue sample by heating at a temperature in the range from 45° to 60° C. to produce a liquid fat;

b) mixing the liquid fat with a water-soluble solvent for the androstenone at the temperature of the liquid fat;

c) cooling the fat/solvent mixture to a temperature at which considerable proportions of the fat dissolved in the solvent are separated out of the solution, and the predominant part of the androstenone dissolved in the solvent phase remains dissolved in the solvent;

d) removing the androstenone-containing solvent phase and diluting in an aqueous buffer solution which is suitable for the detection process used;

e) measuring the androstenone content in the solvent/buffer solution phase by means of competitive immunological detection reactions.

2. Process according to claim 1, wherein the solvent has good dissolving properties for the androstenone to be detected in a temperature range from about 20° to about 60° C. and a temperature coefficient for the fat solubility which is larger than the temperature coefficient in this temperature range for the androstenone solubility.

3. Process according to claim 1, wherein enzymes are used in the detection reaction system and the solvent has, at the most, a small effect on the enzymes.

4. Process according to claim 1, wherein the solvent has at the most a slight effect on antigen/antibody reactions of the detection reaction system.

5. Process according to claim 4, wherein the solvent comprises up to 100% by volume methanol.

6. Process according to claim 1, wherein a mixing ratio of the liquid fat sample to the solvent is chosen in the range from 0.1:10 to 1:10 ratio by volume.

7. Process according to claim 6, wherein the mixing ratio is chosen in the range from 0.2:10 to 0.5:10.

8. Process according to claim 1, wherein the dilution of the solvent phase is carried out with buffer solution in the ratio from 20:80 to 5:95 by volume.

9. Process according to claim 1, wherein in the cooling step, the final temperature of the sample is chosen so that the dissolved fat is separated out of the solvent to such an extent that an essentially fat phase-free solution is obtained in the subsequent dilution step d).

10. Process according to claim 1, wherein in step e)
  (1) a receptacle plate is coated with an antibody serum, and the antibodies are immobilized on the receptacle plate, with the antibodies reacting specifically with androstenones;
  (2) the immobilized antibodies are incubated simultaneously with an enzyme-labeled androstenone and with the solvent-containing buffer solution obtained in step d) at a temperature of about 42° to 48° C.,
  (3) the unbound enzyme-labeled and free androstenone is removed and the coated receptacle plate is washed;
  (4) a buffer solution containing a substrate is placed on the receptacle plate, whereupon the substrate enters into an enzyme reaction with a marker enzyme;
  (5) the enzyme reaction is carried out for a predetermined time at a predetermined temperature and then stopped with a suitable reaction; and
  (6) determining the reaction conversion of the enzymatic reaction.

11. Device for carrying out a process according to claim 1, comprising a heatable sample input station for receiving and liquefying the adipose tissue sample;
having a temperature-controllable, programmable pipetting device with a plurality of sample reception devices for carrying out process steps b), c) and d) according to claim 1 and, optionally, additional steps according to process step e) of claim 1 in which
  (1) antibodies which react specifically with androstenones and which are immobilized on a receptacle plate are incubated simultaneously with a defined amount of an enzyme-labeled androstenone and with a predetermined volume of the solvent-containing buffer solution obtained in step d) at a temperature of about 42° to 48° C., for a predetermined time;
  (2) the unbound enzyme-labeled and free androstenone is removed and the coated receptacle plate is washed;
  (3) a buffer solution containing a substrate is placed on the receptacle plate, whereupon the substrate enters into an enzyme reaction with a marker enzyme;
  (4) the enzyme reaction is carried out for a predetermined time at a predetermined temperature an then stopped with a suitable reaction; and
having a measuring device for direct or indirect determination of a measured variable reflecting the androstenone content of the adipose tissue sample.

12. The process of claimed in claim 10, wherein in step (1) of claim 10, a receptacle plate is coated with an antibody serum and the antibodies are immobilized on the receptacle plate, with the antibodies reacting specifically with 5α-androst-16-en-3-one.

13. The process as claimed in claim 10, wherein in step (1) of claim 10, a receptacle plate is coated with an antibody serum, and the antibodies are immobilized on the receptacle plate, with the antibodies reacting specifically with 5α-androst-16-en-3-one, and in step (2) of claim 10, the temperature is about 45° C.

14. The process as claimed in claim 10, wherein step c) is determined by photospectrometry.

* * * * *